United States Patent [19]

Brunke et al.

[11] Patent Number: 4,753,924

[45] Date of Patent: Jun. 28, 1988

[54] PROCESS FOR THE PREPARATION OF 4,4,7-TRIMETHYL-3,4,7,8-TETRAHYDRO-2(6H)-NAPHTHALENE-ONE

[75] Inventors: Ernst-Joachim Brunke, Holzminden; Ludwig Tumbrink, Höxter, both of Fed. Rep. of Germany

[73] Assignee: Dragoco Gerberding & Co. GmbH, Fed. Rep. of Germany

[21] Appl. No.: 860,812

[22] Filed: May 8, 1986

[30] Foreign Application Priority Data

May 10, 1985 [DE] Fed. Rep. of Germany ....... 3516931

[51] Int. Cl.$^4$ .............................................. A61K 7/46
[52] U.S. Cl. ...................... 512/15; 426/538; 131/276
[58] Field of Search ............... 568/374; 252/522 R; 512/15; 426/538; 131/276

[56] References Cited

U.S. PATENT DOCUMENTS 3,211,157 10/1965 Rowland ............................ 131/276
3,217,717 11/1965 Roberts ............................. 131/276
3,217,718 11/1965 Roberts ............................. 131/276
3,655,720 4/1972 Liffingwell ........................ 568/374

OTHER PUBLICATIONS

Roberts et al., Chem. Abst., vol. 78, #2099y (1973).

Primary Examiner—James H. Reamer
Attorney, Agent, or Firm—Robbins & Laramie

[57] ABSTRACT

4,4,7-trimethyl-3,4,7,8-tetrahydro-2(6H)-naphthalenone is obtained by an elimination reaction from 3-oxo-α-ionol by way of direct addition thereof to a solution of a protonic acid in an inert solvent at an elevated temperature, or following its conversion into a low-carbon alkyl ester, particularly acetate, by way of the treatment of the latter, preferably with sodium acetate, in a polar non-protonic solvent at 150°14 300° C., wherein the output can be increased by raising the temperature of reaction. The product of the process is suitable, in pure form or as mixed with simultaneously produced 3,5,5-trimethyl-4-butenylidene-cyclo-hex-2-en-1-one, as an odiferous substance or as a fragrant substance for foods and tobacco.

4 Claims, 4 Drawing Sheets

PROCESS FOR THE PREPARATION OF 4,4,7-TRIMETHYL-3,4,7,8-TETRAHYDRO-2(6H)-NAPHTHALENE-ONE

FIELD OF THE INVENTION

The invention relates to the bicyclic ketone component. 4,4,7-trimethyl-3,4,7,8-tetrahydro-2(6H)-naphthalen-one, which is useful as an odiferous substance or as a fragrant substance for food and tobacco and the novel processes for its preparation.

BACKGROUND OF THE INVENTION

Chromatographic and spectroscopic methods contribute to the detection of increasingly more and more fragrant substances used for aromatizing foods and semi-luxuries such as tobacco, and odiferous substances utilized in the cosmetic industry. The chemical structure of these substances is determined and their synthetic production follows if required. A major part of the research is done on fragrant components of various kinds of tobacco. A review of a large number of such tobacco components can be found in a paper by C. R. Enzell, J. Wahlberg, A. J. Aasen, in Fortschritte der Chemie Organischer Naturstoffe, vol. 34. Springer-Verlag, Vienna and New York (1977) p. 1–79. An important sensor-active group of those natural fragrant tobacco components are carotenoid derivatives. Within this group, a key compound is 3-oxo-α-ionol (formula 1 below), isolated from tobacco by A. J. Aasen, B. Kimland and C. R. Enzel (Acta Chem. Scand., 25, 1481–1482 (1971)), due to the fact that the compound can be used as a starting material to obtain other derivatives (compare Enzell et al. referred to hereinabove). Such derivatives are, among others, dehydration products resulting from (1) and designated by numerals (2) thru (6), which have also been detected in tobacco (compare A. J. Aasen, B. Kimland, S.-O. Almquist and C. R. Enzell, Acta Chem. Scand., 26, 2573–2576 (1972), the publication being referred to as Reference A hereinafter). A term "megastigmatrienones" was proposed by the above authors to name these products.

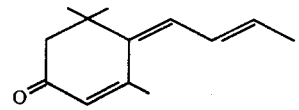

1

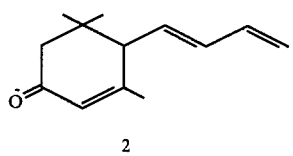

2

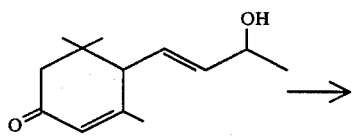

3

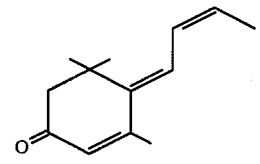

4

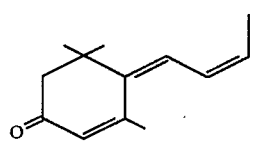

5

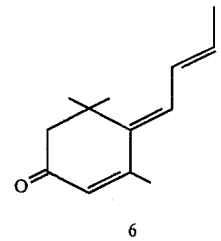

6

The megastigmatrienones (3) thru (6) have also been detected in the "kudzu" (*Puerania lobata*) essential oil by S. Shibata et al. (J. Agric. Biol. Chem., 42, 195–197 (1978)) and as an ingredient of liquid components of "kukoshi" berries (*Lycium chinense M.*) by A. Sannai et al. (J. Agric. Biol. Chem., 47, 2397–2399 (1983)).

The first synthesis of the megastigmatrienones (3) thru (6) was described as early as 1963 (U.S. Pat. No. 3,211,157 to R. L. Rowland), i.e. long before these substances were known to be tobacco components (see Reference A). The synthesis involved the reduction of dehydro-α-ionone (7) with sodium borohydride to alcohol (8) which was then converted into an allyl alcohol (9) using 2N sulfuric acid. The allyl alcohol (9) was then oxidized, using manganese dioxide, to give the megastigmatrienones (3) thru (6).

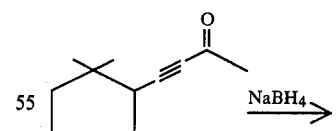

7

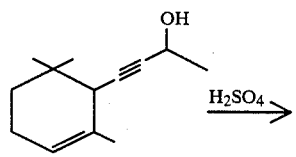

8

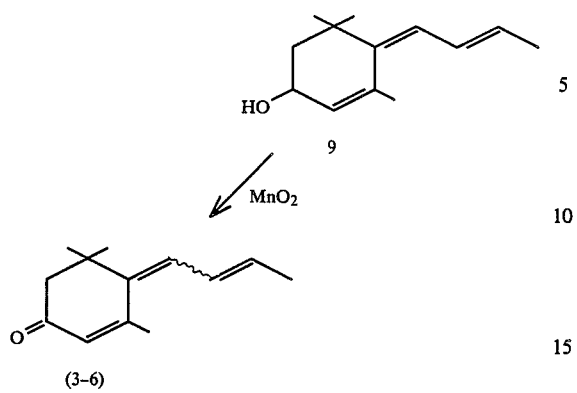

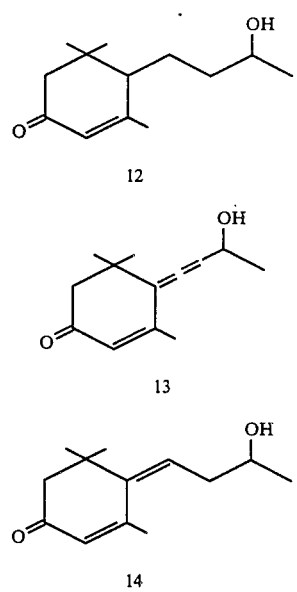

E. Demole and P. Enggist (Helv. Chim. Acta, 57, 2087–2089 (1974)) describe a synthesis starting from a ketoketal (10) obtained from oxo-isophoron. The ketoketal (10) was subjected to exchange reactions with dianion of but-3-in-2-ol and subsequently with lithium aluminium hybride to yield a mixture of megastigmatrienones (3) thru (6) with various hydroxy ketones of megastigmic type (11) thru (14).

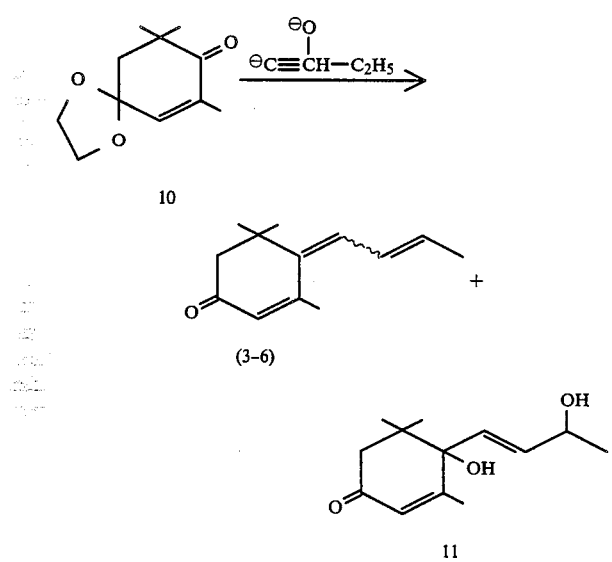

S. Torii, T. Inskuchi and H. Ogawa (Bull. Chem. Soc. Japan, 52, 1233–1234 (1979)) started from dimedone (15). They obtained enolized diketones (16) by aldol condensation of the enolate with crotonaldehyde and subsequent dehydration. The diketones were subjected to exchange reaction with methyllithium and megastigmatrienones (3) thru (6) were obtained.

B. M. Trost and J. L. Stanton (J. Amer. Chem. Soc., 97, 4018–4025 (1975)) reduced 3,4-dehydro-β-ionone (17), and obtained, through subsequent dehydration and sulfenylation, a compound (18) which was converted into the megastigmatrienones (3) thru (6) by way of a sulfenate-sulfoxide rearrangement.

O. Takazwawa, H. Tamura, K. Kogami and K. Hayashi (Bull. Chem. Soc. Japan, 55, 1907–1911 (1982)) described a synthesis of the megastigmatrienones (3) to (6) using isophorone (19) as a starting compound. Isophorone trimethylsilyl enol ether (20 a) was condensed with crotonaldehyde to give oxo-damascol (20 b). The latter was dehydrated, resulting in a mixture of megastigmatrienones (3) to (6).

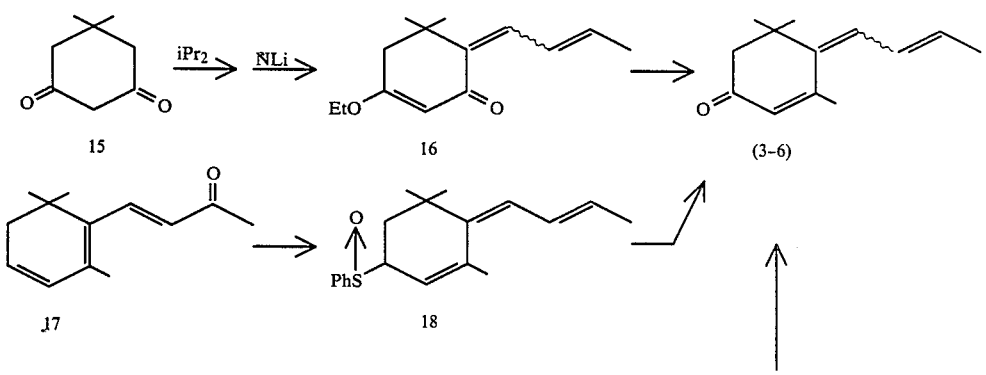

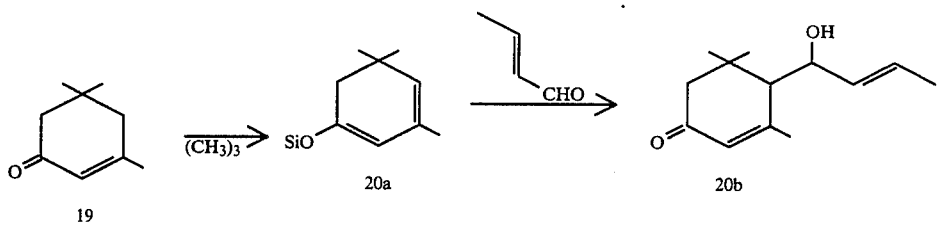

The acid-catalyzed dehydration of 3-oxo-α-ionol (1) is known so far to have been described only once in technical literature. Aasen, Kimland, Almquist and Enzell (see Reference A) heated 3-oxo-α-ionol (1) together with potassium bisulfate at 100° C., solvent-free, or with p-toluene sulfonic acid (benzene as solvent, under reflux) for 2 to 3 hours. As a result, a mixture of isomeric megastigmatrienones (2) to (6) was obtained at all times. The proportion of the respective isomers in the mixture was determined using gas chromatography to be (2):(3):(4):(5):(6) = 10:1:10:1:10

According to Reference A, a similar mixture of final compounds can be obtained under the above conditions starting from an acetate prepared from compound (1). However, experimental details have not been disclosed.

SUMMARY OF THE INVENTION

The invention relates to the bicyclic ketone compound 4,4,7-trimethyl-3,4,7,8-tetrahydro-2(6H)-naphthalen-one, which is suitable as an odiferous substance or as a fragrant substance for food and tobacco.

The invention further relates to process for the production of 4,4,7-trimethyl-3,4,7,8-tetrahydro2(6H)-naphthalen-one by an elimination reaction from 3-oxo-α-ionol by way of direct additive thereof to a solution of a protonic acid in an inert solvent at an elevated temperature, or following its conversion into a low-carbon alkyl ester, particularly acetate, by way of the treatment of the latter, preferably with sodium acetate, in a polar non-protonic solvent at 150°-300° C., wherein the output can be increased by raising the temperature of reaction.

More particularly the present invention relates to the production of 4,4,7-trimethyl-3,4,7,8-tetrahydro-2(6H)-naphthalen-one of the formula

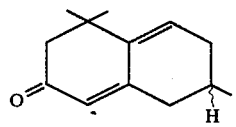

in pure form or as mixed with 3,5,5-trimethyl-4-butenylidene-cyclo-hex-2-en-1-one of the general formula

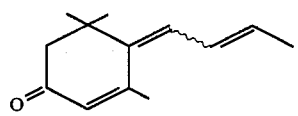

wherein 3-oxo-α-ionol of the formula

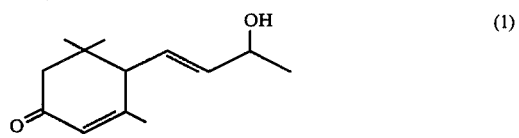

is subject to an elimination reaction either by adding 3-oxo-α-ionol to the solution of a protonic acid in an inert solvent at an elevated temperature and separation of water of reaction in a conventional way, or by converting 3-oxo-α-ionol into its low-carbon alkyl ester and treating the latter with hydroxides or acetates of alkali metals or alkaline-earth metals in a non-protonic solvent at temperatures of 150° to 300° C. The 4,4,7-trimethyl-3,4,7,8-tetrahydro-2(6H)-naphthalen-one, if necessary, is separated from the resulting mixture for enrichment or rectification.

When the 4,4,7-trimethyl-3,4,7,8-tetrahydro-2(6H)-naphthalen-one is accompanied by 3,5,5-trimethyl-4-butenylidene-cyclo-hex-2-en-1-one the latter is cyclized, before or after the separation of the naphthalen-one produced heretofore, to yield further amounts of the 4,4,7-trimethyl-3,4,7,8-tetrahydro-2(6H)-naphthalen-one by extending the reaction involving the conversion of 3-oxo-α-ionol into its low-carbon-alkyl ester by treating the latter with hydroxides or acetates of alkali metals or alkaline-earth metals under analogous conditions.

In the description of hitherto-conducted syntheses (i.e. syntheses of prior art) of the megastigmatrienones (2) and (3) thru (6), no remark can be found about bicyclic by-products which is particularly remarkable in view of the comprehensive and detailed work of Enzell et al. (see Reference A) wherein monocyclic compounds (2) thru (6) only were obtained by dehydration of 3-oxoα-ionol (1). Dehydration of α-ionol by F. B. Whitfield and G. Sugowdz, (Aust. J. Chem., 35, 591–600 (1982)) also resulted in monocyclic products only.

At that stage, it was discovered, surprisingly, that 3-oxo-α-ionol can be converted under specific process conditions into 4,4,7-trimethyl-3,4,7,8-tetrahydro-2(6H)-naphthalen-one (compound (21)) which was mentioned in the literature only once so far, namely by D. L. Roberts and W. A. Rohde (Tob Sci., 16, 107-112 1972)), hereinafter referred to as Reference B) who described the ketone (21) as a component of Burley tobacco. D. L. Roberts and W. A. Rohde isolated compound (21) using column chromatography and gas chromatography. No synthesis of compound (21) is known to have been described thus far. As shown in the following reaction diagram and explained below in more detail, dehydration of (1) using the reagents described by Enzell et al. in Reference A but with an inverse reaction course results in a mixture of products including megastigma trienones (3) to (6) and up to about 10% of the bicyclic ketone (21).

According to the invention, it is also possible to convert a 3-oxo-α-ionol low-carbon alkyl ester obtained in a conventional way from compound (1), for instance 3-oxo-α-ionol acetate (22) into a mixture of (3) thru (6) and (21). It can be accomplished preferably with the use of sodium acetate in polar non-protonic solvents, wherein the formation of compound (2) is very strongly suppressed. The percentage of bicyclic ketone (21) in the mixture can be stepped up by increasing the temperature.

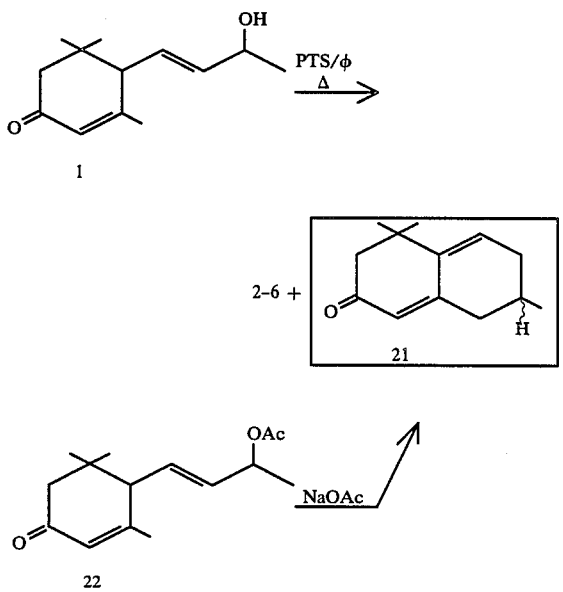

BRIEF DESCRIPTION OF THE DRAWINGS

The invention is further explained by the accompanying drawings in which.

DETAILED DISCLOSURE

Figure 1:
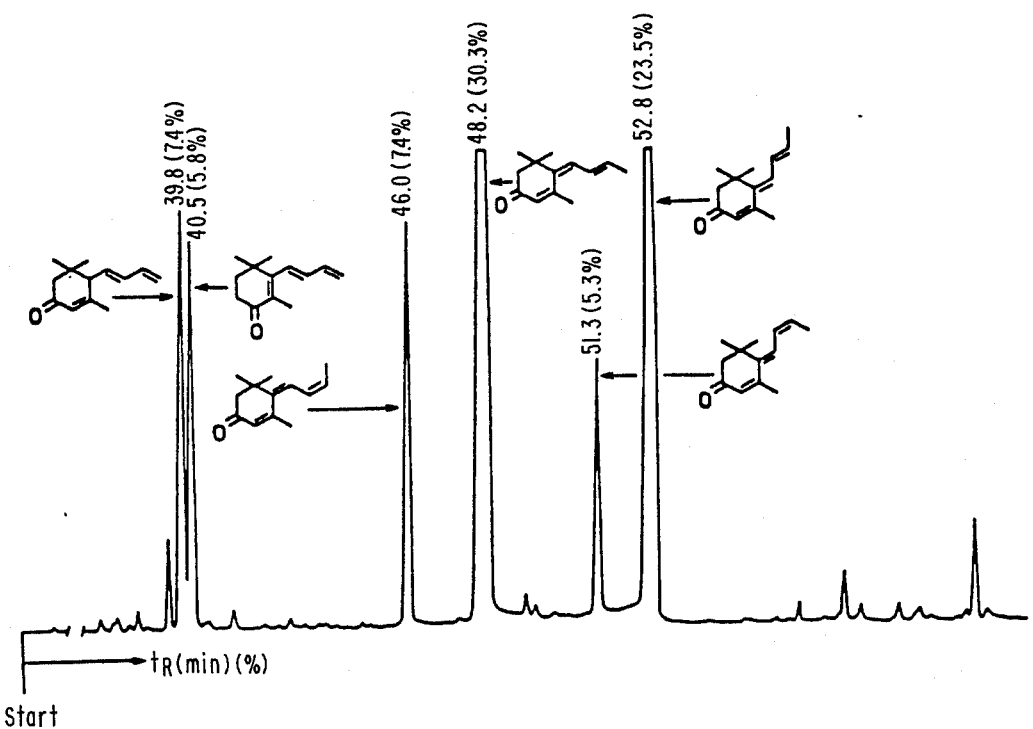
FIG. 1 is a gas chromatogram of the mixture of products obtained according to a prior art method (see Example 1)

The invention is also explained in more detail by the examples set forth below. In the Example A, the reaction conditions given in Reference A have been repeated. Thus, a mixture of compound (1) and potassium bisulfate was heated at 100° C. resulting in the dehydration of (1) and the formation of the megastigmatrie-nones (2) thru (6) that were mentioned in Reference A, though at a somewhat reduced concentration (see gas chromatogram in FIG. 1). A further study showed that a similar mixture was obtained when a solution of (1) and p-toluenesulfonic acid was boiled in benzene under dehydrating conditions.

It was found, however, that the reaction conditions specified by Enzell et al. in Reference A for preparing the mixture of (2) and (3) . . . (6) from 3-oxo-α-ionol and its acetate (22), that is heating the ionol with KHSO$_4$ in dry state or toluene, were applicable for compound (1) only and not for the acetate (22). Further studies showed that when the compound (22) was heated with potassium bisulfate at 100° C. or boiled with p-toluenesulfonic acid in benzene, unchanged substrate was recovered exclusively.

Figure 2:
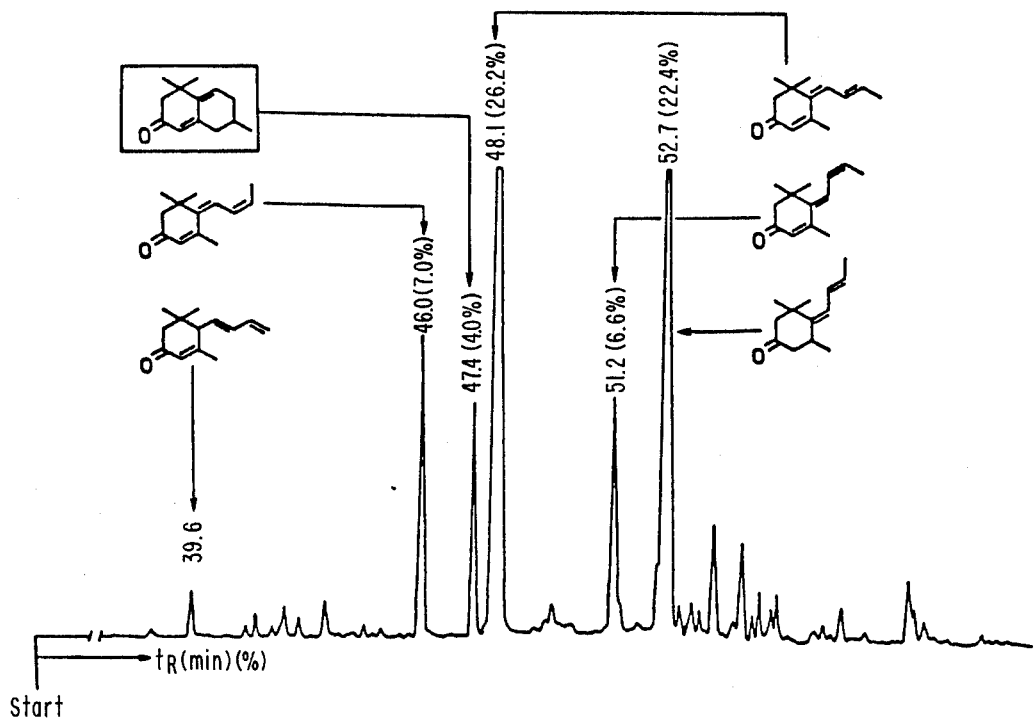
FIG. 2 is a gas chromatogram of the mixture of products obtained from 3-oxo-α-ionol according to the invention (see Example 2)

As shown in Example 2, an inverse course of reaction according to the invention, i.e. adding dropwise the solution of 3-oxo-α-ionol (1) to a boiling solution of the acid results unexpectedly in a production of larger portions of the bicyclic ketone (21) in addition to the monocyclic ketones (2) thru (6). Simultaneously, the amount of the ketone (2) is considerably reduced, as seen in the chromatogram of FIG. 2. It appears, further, that the proportion of the bicyclic ketone (21) can be increased through a rise in temperature, for instance by maintaining the reaction at the boiling temperature, e.g. by using boiling xylene as solvent.

The reaction can also be carried out using other arylsulfonic acids (e.g. benzenesulfonic acid, p-bromobenzenesulfonic acid) or acid ion exchangers in various aromatic solvents (e.g. benzene, toluene, xylene, chlorobenzene, nitrobenzene) or high-boiling ethers (e.g. diethylene glycol dimethyl ether, ethylene glycol dibutyl ether).

As shown in Examples 3 and 4, the 3-oxo-α-ionol acetate (22) produced from compound (1) in a conventional way can also be converted into a mixture of (3) to (6) and (21). This process being carried out, advantageously, with the use of sodium acetate in polar non-protonic solvents. When sodium acetate/ethyleneglycol mixture is used at 180° C. (Example 3), a mixture containing ca. 15% of compound (21) is obtained (see gas chromatogram of FIG. 3).

The proportion of the bicyclic ketone (21) can be increased by increasing the temperature of the reaction, e.g., by using a high-boiling solvent. When a mixture of sodium acetate and ethylene glycol is used at 200° C. (Example 4), the resulting product mixture contains ca. 70% of compound (21) (see gas chromatogram in FIG. 4). Reaction conditions analogous to those above may also be applied in order to cyclize the mega-stigmatrienones (3) thru (6) to obtain the compound (21).

Other suitable reagents include hydroxides or salts of low alkanecarboxylic acids, the metals being other alkali metals or alkaline-earth metals, e.g., sodium hydroxide, sodium propionate, potassium hydroxide and potassium acetate.

Suitable solvents comprise high-boiling ethers, e.g., ethylene glycol dibutyl ether or diethylene glycol dimethyl ether, or corresponding high-boiling gasoline fractions.

It is also possible, if necessary, to cyclize the 3,5,5-trimethyl-4-butenylidene-cyclo-hex-2-en-1-one which accompanies 4,4,7-trimethyl-3,4,7,8-tetrahydro-2(6H)-naphthalen-one, before or after the separation of the former, to yield further amounts of 4,4,7-trimethyl-3,4,7,8-tetrahydro-2(6H)-naphthalen-one by extending the reaction time (5–10 h) in the presence of hydroxides or acetates of alkali metals or alkaline-earth metals at elevated temperatures, preferably from 150° to 300° C.

As can be seen from Example 5, a drastic rise in reaction temperature without the use of reagents, e.g., a pyrolysis of the acetate (22) at ca. 500° C. results in the formation of megastigma-trienone (2) only. In order to produce the bicyclic ketone (21) from (1) or (22), the presence of acids or bases seems to be necessary apart from a certain temperature elevation.

The ketone (21) synthesized according to the invention can be enriched or produced in a pure form using conventional methods like fractional distillation as well as preparative-scale gas chromatography or column chromatography, also under elevated pressure (HPLC).

affects adversely the use of such mixtures as odoriferous or fragrant substances.

The ketone (21), on the other hand, possesses characteristic and decidedly highly-rated gustatory and olfactory qualities which could not have been expected on the grounds of the presence of (21) in tobacco. The "faint woody" aroma properties of (21) indicated in Reference B apply merely to the fragrance of tobacco. The properties were tested in conjunction with an unspecified tobacco and there is nothing in that Reference regarding the purity of the isolated natural ketone (21).

As shown in Table 2, the presence of (21) beside the mega-stigmatrienones (3) thru (6) endows such mixtures with clearly improved properties.

TABLE 2

| | Olfactory and gustatory properties of compounds (2), (3) thru (6) and (21) | | |
|---|---|---|---|
| | Odor (10% on the smelling test strip) | Taste (0.5 ppm in sugar sweetened water) | Taste (0.005% in tobacco American blend type |
| 2 (from Example 5) | herbal "green" slightly oily | oily, "green" fruity | generally suppressed tobacco effects: tobacco-unrelated "green" type: after-taste of fenugreek. |
| 3-6 (Example 1) | dry fruits, reminiscent of hay, woody, tobacco aspects. | strong fruity, balmy, tobacoo aspects. | fuller, no foreign-to-tobacoo type, but still reduced "flue-cured" quality. |
| 21 (Example 4) | soft, herbal, butter-milky (lactone-type) | soft, fruity, some milk/cream aspects, slightly woody. | reduced tongue-burning, intensified mouth-filling, more body, increased inhalation effect; stronger tar and hay-like tinge; no tobacco-unrelated qualities. |
| 21+ 3-6 (Example 3) | sweet - balmy, typical tobacco flavour, soft-woody (sandalwood), dry-fruit/honey features. | sweet fruity, hebal, buttery, honey-like (mouth-filling similar to warm milk) | more fill and taste, harmonious smoke, distinct sweetness, stronger typical "American blend" character; no features foreign to tobacco. |

As shown in Table 1, spectroscopic data for the isolated synthetic ketone (21) correspond largely to the data pertaining to the natural substance, disclosed in Reference B.

TABLE 1

| Spectroscopic data for (21) | | |
|---|---|---|
| | Natural substance (according to Ref. B) | Synthetic product (acc. to invention) |
| IR, γ (cm$^{-1}$) | 1660,1622,1596 1300,1250 | 1665,1625,1595 (FIG. 5) 1300,1250 |
| UV, λmax (ε') | 287 (90.3) | 289 (57.5) (FIG. 6) |
| $^1$H-NMR (solvent ?) δ [ppm] | 5.95 (1H) 5.62 (1H) 2.20 (3H) 1.20 (3H) 1.15 (3H) 1.03 (2H, d) | (CCl$_4$) 5.9–6.1 (1H) (FIG. 7) 5.53 (1H) 2.21 (3H) 1.18 (3H) 1.13 (3H) 1.04 (2H, d) |
| MS, m/e | 190 (M$^+$) | 190 (M$^+$) (FIG. 8) |

The testing of olfactory and sensory properties of (21) and mixtures of (21) with (3) thru (6) revealed that megastigma-trienone (2) with deconjugated double bonding system (see Example 5 for preparation procedure) has less desirable olfactory and sensory properties. Hence, the presence of that compound in the mixture of products of elimination of 3-oxo-α-ionol (1)

Thus, the bicyclic ketone (21) and its mixtures with the megastigmatrienones (3) to (6), wherein isomer (2) is avoided to a large extent, prove advantageous as odoriferous substances or components of perfume oils for cosmetic, commercial and technical applications as well as fragrant substances or components of such mixtures useful for foods and semi-luxuries such as tobacco and tobacco products.

The invention is explained by the following examples without being limited thereto. The term "gas chromatogram" is abbreviated as GC.

Example 1 (reference example)

Dehydration of 3-oxo-α-ionol (1) using potassium bisulfate (a) 10 g of 3-oxo-α-ionol (1) were mixed with 5 g of powdered potassium bisulfate and heated at 100° C. with stirring. After 8 hours of stirring at 100° C. the mixture was cooled down to room temperature and 100 ml of water was added. Multistage extraction with naphtha, neutral washing of the combined organic phase with a sodium bicarbonate solution and boiling down under reduced pressure followed. A total of 8.1 g of product mixture was obtained; see gas chromatogram in FIG. 1.

(b) A solution of 10 g of 3-oxo-α-ionol (1) in 100 ml of toluene was compounded with 5 g potassium bisulfate and heated under reflux for 14 hours. The mixture was then cooled down to room temperature and washed with water and a sodium bicarbonate solution. The solvent was distilled off under reduced pressure. A total of 7.9 g of product mixture was obtained. Gas chromatogram: GC column made by W. Guenther, Duesseldorf (25 m glass capillary tube, stationary phase WG 11, temperature program: 160°–220° C., 10° C./min): $t_r$ (min)=9.1 (26% (2)), 10.4, 10.8, 11.4, 11.7, (2.1%, 23.7%, 3.6%, 30.4%, (3)–(6)); no (21) at $t_r$=10.4 min.

Example 2

Dehydration of 3-oxo-α-ionol (1) using para-toluenesulfonic acid 300 g of 3-oxo-α-ionol (1) was added dropwise within 1 hour to a solution containing 6 g of para-toluenesulfonic acid in 900 ml of toluene, the solution being boiled in a water separator. It was then allowed to cool down to room temperature and neutral-washed with water and a sodium carbonate solution. The mixture was then concentrated and distilled using a 20 cm Vigreux column. 140 g of product mixture containing (2) thru (6) and (21) was obtained. Boiling point (1 mbar)=100°–120° C. (gas chromatogram in FIG. 2).

Example 3

Elimination reaction with 3-oxo-α-ionol acetate (22) at 180°–190° C.

100 g 3-oxo-α-ionol acetate (22) was added dropwise, with stirring, to a solution of 16 g anhydrous sodium acetate in 168 g ethylene glycol at 180°–190° C. within 1 hour. Acetic acid formed was distilled off. After two hours of agitating at 180°–190° C. the reaction mixture was allowed to cool, diluted with water and extracted with toluene. The combined organic phase was dried and concentrated under reduced pressure whereby 70 g of raw product was obtained. Subsequent distillation through a 20 cm Vigreux column yielded 35 g of product mixture containing (2) thru (6) and (21); b.p. (1 mbar)=100°–140° C. See FIG. 3 for gas chromatogram.

A solution of 5 g of the above-defined product mixture (2 to 6) and (21) in 10 ml of ethylene glycol and 1 g of sodium acetate was agitated for 16 hours at 200° C. A common processing was applied which resulted in a raw product containing up to about 70% of (21) according to GC. The ketone (21) was isolated by means of a column chromatograph with 100 g of silicagel (length 130 cm, diameter 2 cm; grain size 0.063–0.20 mm; eluent carrier-cyclohexane/ethyl acetate 4:1); purity 95% according to GC; IR spectrum shown in FIG. 5, UV spectrum in FIG. 6, $^1$H-NMR spectrum in FIG. 7 and mass spectrum in FIG. 8.

Example 4

Elimination reaction of 3-oxo-α-ionol acetate at 200°–220° C.

150 g 3-oxo-α-ionol acetate (22) was added dropwise within one hour to a solution of 24 g of anhydrous sodium acetate in 250 g ethylene glycol at a temperature of 200°–220° C. with stirring. Acetic acid formed was distilled off. After two hours of agitating at 200°–220° C., the mixture was allowed to cool down to room temperature, diluted with water and extracted with toluene. Subsequently the combined organic phase was neutral washed and concentrated to yield 98 g of raw product. After distillation through a 20 cm Vigreux column, 53.5 g of bicyclic ketone (21) of 70% purity (according to GC) was obtained; b.p. (0.2 mbar)=95°–125° C. Gas chromatogram shown in FIG. 4; output 32.8%. Distillation through an 80 cm column with metal packing yielded 35 g of compound (21) of 90% purity (according to GC).

Example 5

Pyrolysis of 3-oxo-α-ionol acetate (22)

50 g 3-oxo-α-ionol acetate (22) was passed through a vertical 50 cm-long glass tube filled with glass packing (Raschig rings 5 mm dia.) during a two-hour period, wherein acetic acid formed was distilled off under slightly reduced pressure. The reaction product was collected in a flask. The raw product was distilled through a 20 cm Vigreux column and 26.3 g of the ketone (2) of ca. 80% purity (according to GC) was obtained. Another distillation through a 1 m spinning band column produced 15.6 g of (2) at b.p. (1 mbar)=105° C. $^1$H-NMR (CCl$_4$): δ=0.97 and 1.05, 2s(1,1—CH$_3$), 1.90, s(5—CH$_3$), 2.57, "s"(6-H), 5.10 and 5.20, 2m(10, 10-H), 5.56, m(7H), 5.90, "s"(4-H), 6.10, m(8-H), 6.28 ppm, m(9-H).

Example 6

| Perfume base of herbal - woody (ligneous) types | Parts |
| --- | --- |
| Linalol | 10 |
| linalyl acetate | 30 |
| lavender oil, French | 20 |
| bergamot oil, Reggio | 40 |
| 2,2-dimethyl-3-phenyl propanol (Muguet alcohol) | 200 |
| diheptyl acetate | 80 |
| acetyl cedrene (commercial name "Lignofix") | 100 |
| mahagonate | 300 |
| phyllantone N | 20 |
| rosemary oil, 10% solution in dipropylene glycol | 50 |
| oakmoss extract, 10% solution in dipropylene glycol | 30 |
| hyssop oil, Spanish | 10 |
| patchouli oil | 60 |
|  | 950 |

(a) +50 parts of (21) (according to Ex. 4)
(b) +50 parts of (3) thru (6) and (21) (according to Ex. 3)

This perfume base possesses a well-balanced herbal-woody scent with fresh spicy aspects. The addition of ketone (21) makes the overall sensory impression softer and more harmonious and preserves a natural emanation of the composition and also emphasizes its flowery aspects.

Alternatively, the addition of the mixture of (3) thru (6) and (21) enriches the original olfactory impression through a sweet-herbal and a bitter-green tinge and also makes it more harmonious.

Example 7

| Strawberry fragrance | Parts |
| --- | --- |
| amyl acetate | 34.0 |
| amyl butyrate | 15.0 |
| amyl valerate | 15.0 |
| anethole | 1.5 |
| benzyl acetate | 85.0 |
| butyric acid | 15.0 |
| cinnamic isobutyrate | 7.0 |
| cinnamic valerate | 9.5 |
| oenanthic ether | 1.5 |
| diacetyl | 10.0 |
| ethyl acetate | 50.0 |
| ethylamyl ketone | 15.0 |
| ethyl butyrate | 30.0 |
| ethyl cinnamate | 52.0 |

| Strawberry fragrance -continued | Parts |
| --- | --- |
| ethyl heptylate | 2.5 |
| ethyl-methylphenyl glycidate | 260.0 |
| ethyl propionate | 15.0 |
| ethyl valerate | 60.0 |
| hydroxyphenyl-2-butanone (10% soln. in ethanol) | 5.0 |
| β-ionone | 6.5 |
| citral | 1.0 |
| maltol | 70.0 |
| methyl anthranilate | 7.0 |
| methyl cinnamate | 35.5 |
| methyl salicylate | 6.5 |
| neroli oil | 0.5 |
| phenylethyl alcohol | 1.5 |
| γ-undecalactone | 58.5 |
| vanillin | 70.0 |
| triethyl citrate | 1000.0 |
| ethanol | 60.0 |
|  | 2000.0 |

This composition, in conventional strengths, possesses a strong strawberry-like fragrance. If, instead of ethanol, 60 parts of ketone (21) are introduced, the fragrance will be enriched by softer, creamy gustatory aspects which liken the resulting impression to natural strawberry aroma. Alternatively, when the mixture of compounds (3) to (6) and (21) is introduced (Example 3), a favourable modification of the original strawberry aroma is accomplished as more fullness is added but also some woody qualities appear which are reminiscent of strawberry kernels.

Example 8

| "Virginia - Enhancer" tobacco fragrance | Parts |
| --- | --- |
| Angelica (root) oil (1% in propylene glycol) | 5.0 |
| cardamon oil (1% in propylene glycol) | 20.0 |
| bay oil (1% in ethanol) | 10.0 |
| fenugreek extract | 2.0 |
| levisticum oil | 0.5 |
| furfural | 5.0 |
| cumarin | 15.0 |
| vanilla extract (10% in propylene glycol) | 150.0 |
| clove-leaf oil | 5.0 |
| coriander oil | 1.0 |
| amyl isovalerate | 5.0 |
| ethanol | 201.5 |
| propylene glycol | 550.0 |
|  | 970.0 |

At a dosage of 80 g per 100 Kg of tobacco, this composition enhances the dark tobacco character and produces the impression of more mouth-fill when smoking and also emphasizes the spiciness and tar presence. The addition of 30 parts of the mixture (2) thru (6) and (21) (Example 3) creates a fragrance which, at similar strength, has a clearly stronger Virginia tobacco character.

FIG. 1. Gas chromatogram of the mixture of dehydration products according to Example 1 (KHSO₄/100° C.) (60 m glass capillary tube, DB—wax packing, temperature program 100°-200° C., 2° C./min).

FIG. 2. Gas chromatogram of the mixture of dehydration products according to Example 2 (60 m glass capillary tube, DB—wax packing, temperature program 100°-200° C., 2° C./min).

Figure 3:
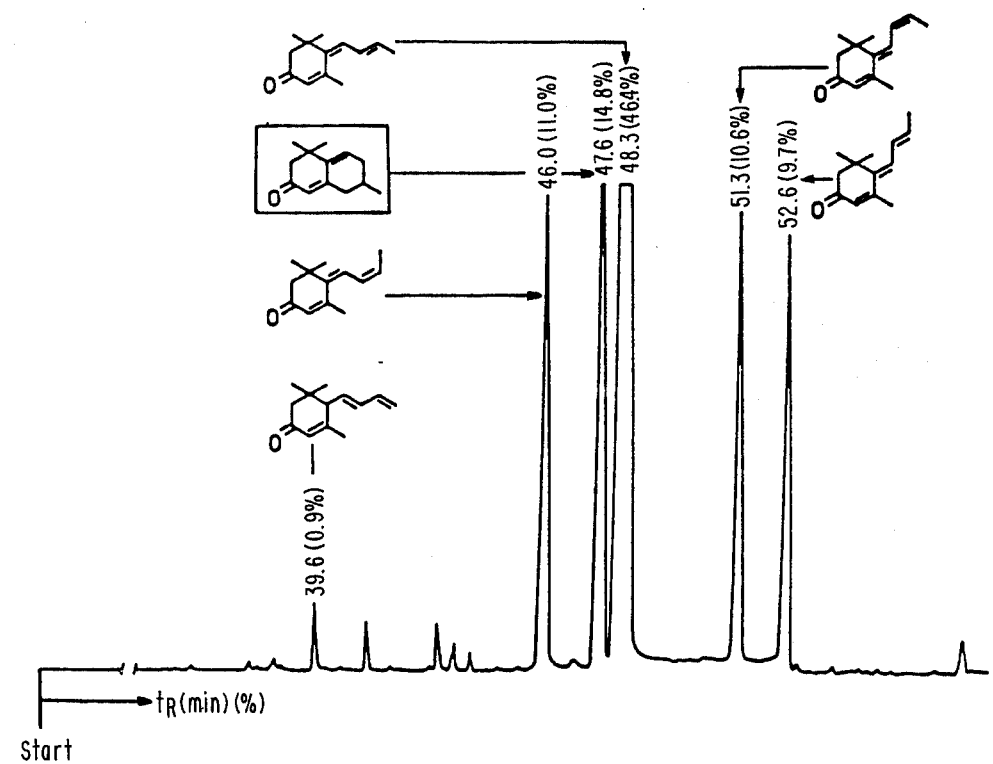
FIG. 3 is a gas chromatogram of the mixture of products obtained from 3-oxo-α-ionol acetate according to the invention (see Example 3)

FIG. 3. Gas chromatogram of the mixture of products according to Example 3 (60 m glass capillary tube, DB—wax packing, temperature program 100°-200° C., 2° C./min).

Figure 4:
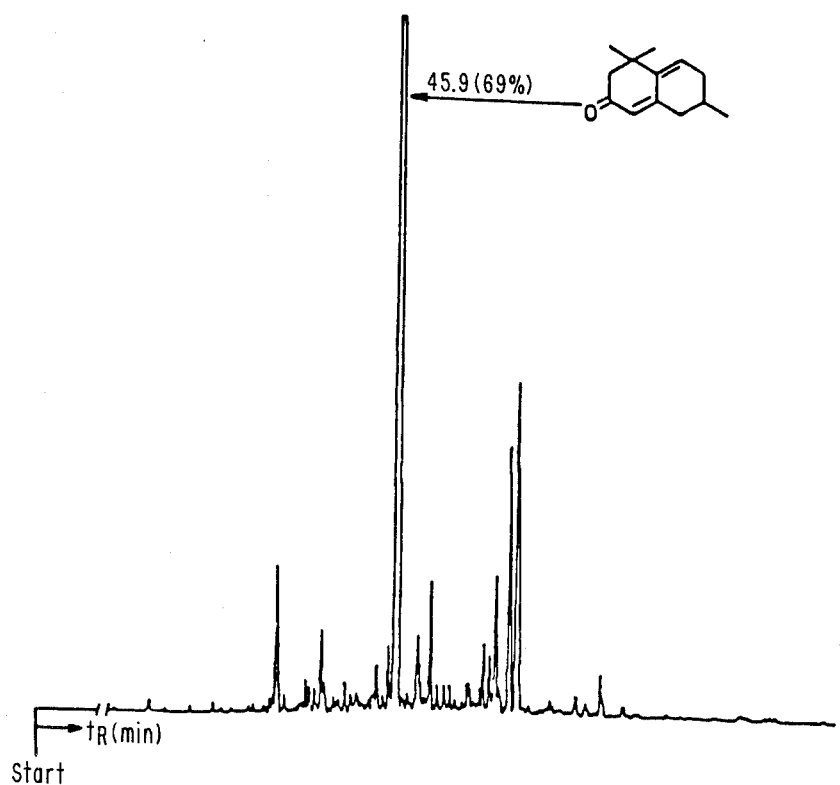
FIG. 4 is a gas chromatogram of the mixture of products obtained from 3-oxo-α-ionol acetate at comparatively high temperature (see Example 4)

FIG. 4. Gas chromatogram of the mixture of products according to Example 4 (30 m glass capillary tube, DB—wax, temperature program 100°-240° C., 10° C./min).

Figure 5:
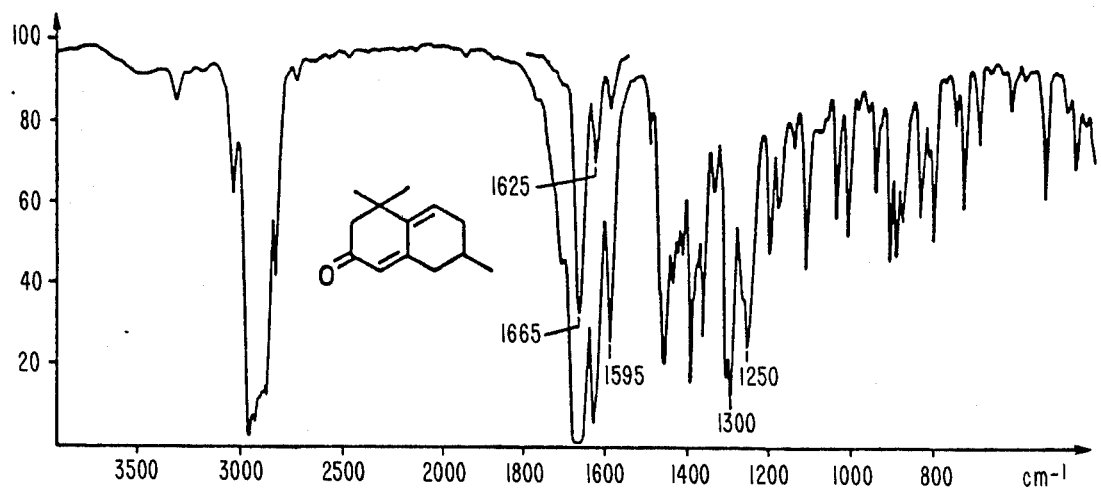
FIGS. 5 thru 8 represent the IR spectrum, UV spectrum, $^1$H-NMR spectrum and mass spectrum respectively of the bicyclic 4,4,7-trimethyl-3,4,7,8-tetrahydro-2(6H)-naphthalen-one (21) obtained according to the invention (see Example 3).

FIG. 5. IR spectrum (film) of (21).

Figure 6:
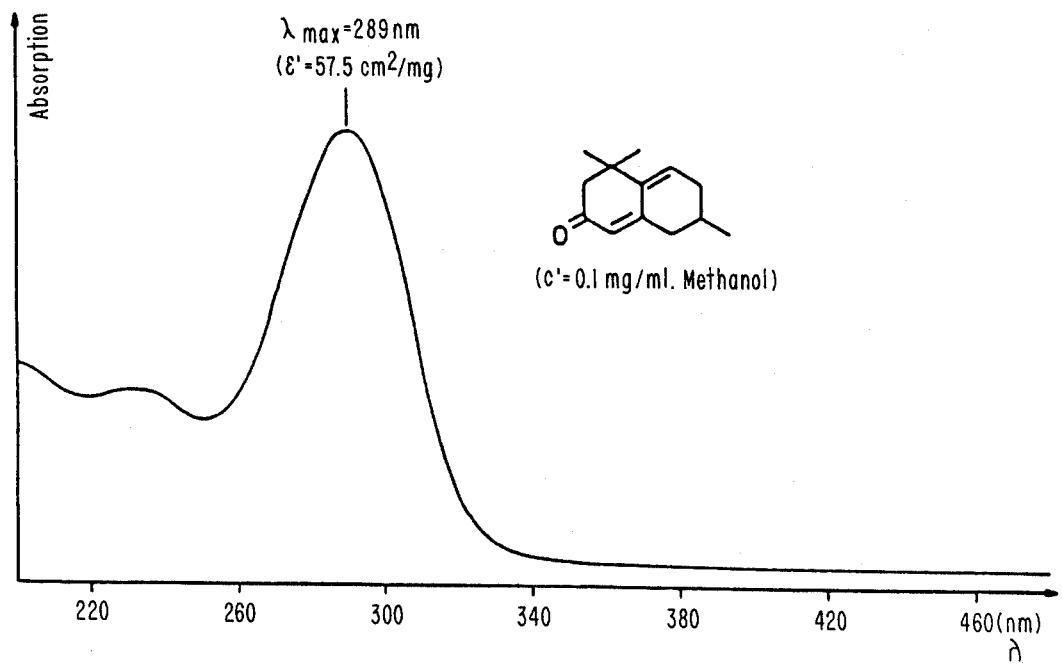

FIG. 6. Uv spectrum (methanol) of (21).

Figure 7:
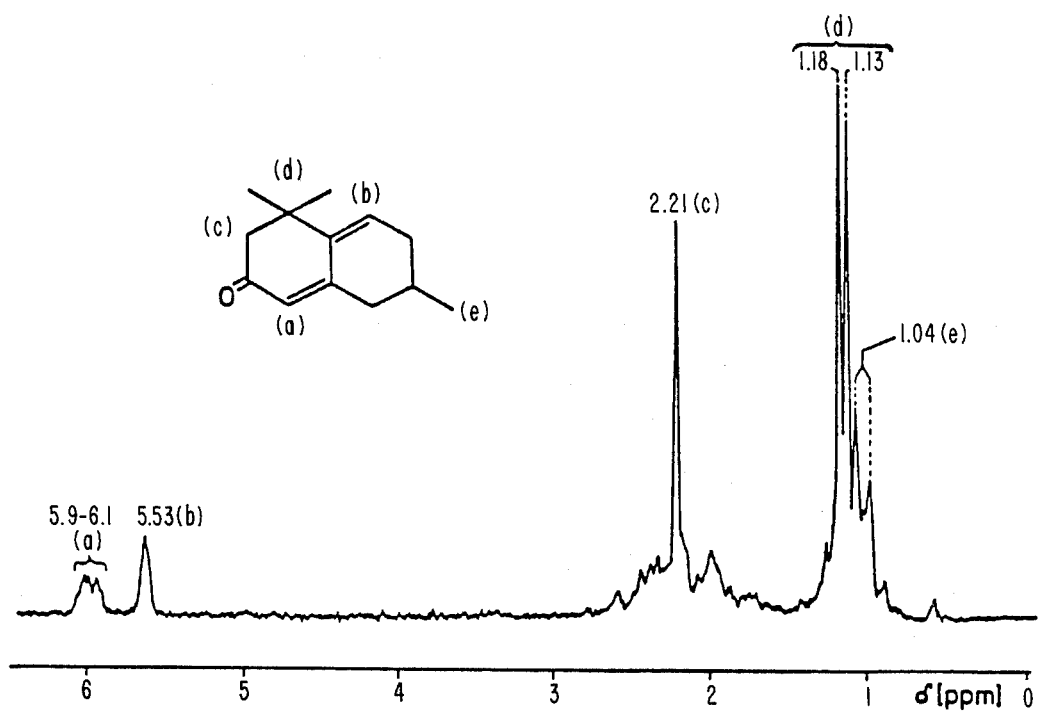

FIG. 7. ¹H-NMR spectrum of (21) (60 mHz, CCl₄, TMS as inner standard).

Figure 8:
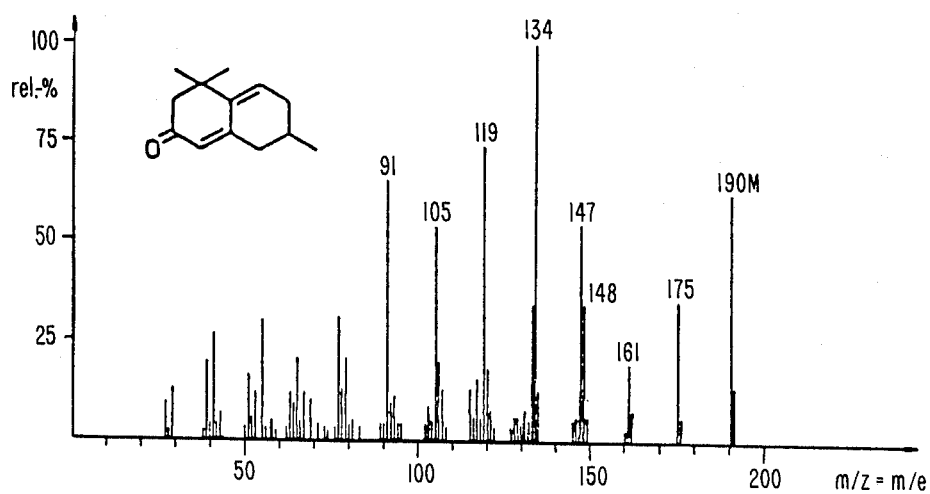

FIG. 8. Mass spectrum of (21) at 80 eV (m/z=m/e (mass/charge)).

We claim:

1. A process for scenting cosmetic goods, commercial goods or technical goods or for aromatizing foods or semi-luxuries which comprises adding a scenting quantity to said cosmetic goods, commercial goods or technical goods or an aromatizing quantity to said foods or semi-luxuries of a synthetic mixture prepared by subjecting 3-oxo-α-ionol of the formula

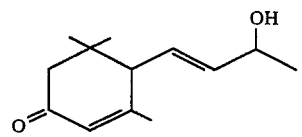

to an elimination reaction to produce 4,4,7-trimethyl-3,4,7,8-tetrahydro-2(6H)-naphthalene-one of the formula

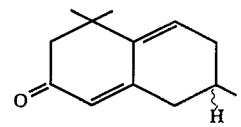

in pure form or mixed with 3,5,5-trimethyl-4-butenylidene-cyclohex-2-en-1-one of the formula

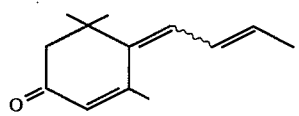

wherein said synthetic mixture contains at least 0.1% of said naphthalene-one.

2. A process for scenting cosmetic goods, commercial goods or technical goods or for aromatizing foods or semi-luxuries which comprises adding a scenting quantity to said cosmetic goods, commercial goods or technical goods or an aromatizing quantity to said foods or semi-luxuries of a synthetic distillation fraction prepared by first converting 3-oxo-α-ionol of the formula

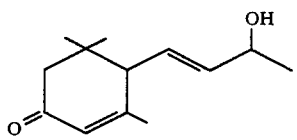

into a low-carbon alky ester and then treating the ester with an alkali metal hydroxide or acetate or an alkaline earth metal hydroxide or acetate in a non-protonic solvent at 180° C. to 230° C. to produce 4,4,7-trimethyl- 3,4,7,8-tetrahydro-2(6H)-naphthalene-one of the formula

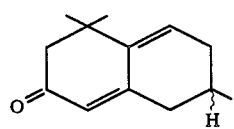

wherein said synthetic distillation fraction contains from 1% to 95% of said naphthalene-one.

3. The process according to claim 1 wherein said synthetic mixture is added to cosmetic goods, commercial goods, technical goods, or foods.

4. The process according to claim 2 wherein said synthetic distillation fraction is added to cosmetic goods, commercial goods, technical goods, or foods.

* * * * *